US010265208B2

(12) United States Patent
Wood et al.

(10) Patent No.: US 10,265,208 B2
(45) Date of Patent: Apr. 23, 2019

(54) RECONSTRAINMENT BAND WITH REDUCED REMOVAL INTERFERENCE

(71) Applicant: BOSTON SCIENTIFIC SCIMED, INC., Maple Grove, MN (US)

(72) Inventors: Mark D. Wood, Shrewsbury, MA (US); John J. Damarati, Marlborough, MA (US); John O. McWeeney, Brighton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 217 days.

(21) Appl. No.: 15/009,449

(22) Filed: Jan. 28, 2016

(65) Prior Publication Data
US 2016/0143761 A1 May 26, 2016

Related U.S. Application Data

(63) Continuation of application No. 12/845,243, filed on Jul. 28, 2010, now abandoned.

(60) Provisional application No. 61/229,976, filed on Jul. 30, 2009.

(51) Int. Cl.
*A61F 2/966* (2013.01)
*A61F 2/95* (2013.01)

(52) U.S. Cl.
CPC ............... *A61F 2/966* (2013.01); *A61F 2/95* (2013.01); *A61F 2002/9505* (2013.01); *A61F 2002/9522* (2013.01); *A61F 2002/9665* (2013.01)

(58) Field of Classification Search
CPC .... A61F 2/95; A61F 2/966; A61F 2002/9505; A61F 2002/9522; A61F 2002/9528; A61F 2002/9534; A61F 2002/9665
See application file for complete search history.

(56) References Cited

U.S. PATENT DOCUMENTS

| | | |
|---|---|---|
| 5,833,632 A | 11/1998 | Jacobsen et al. |
| 6,014,919 A | 1/2000 | Jacobsen et al. |
| 6,258,099 B1 * | 7/2001 | Mareiro ............... A61F 2/958 604/96.01 |
| 6,260,458 B1 | 7/2001 | Jacobsen et al. |
| 6,428,489 B1 | 8/2002 | Jacobsen et al. |
| 6,431,039 B1 | 8/2002 | Jacobsen et al. |
| 2002/0035396 A1 | 3/2002 | Heath |
| 2004/0204749 A1 | 10/2004 | Gunderson |
| 2005/0102020 A1 | 5/2005 | Grayzel et al. |

(Continued)

FOREIGN PATENT DOCUMENTS

| | | |
|---|---|---|
| EP | 0819411 A2 | 1/1998 |
| WO | 0071058 A1 | 11/2000 |

*Primary Examiner* — Robert A Lynch
(74) *Attorney, Agent, or Firm* — Seager, Tufte & Wickhem, LLP

(57) ABSTRACT

The reconstrainment band includes a hollow generally tubular shaped band having proximal and distal ends and having an exterior surface for engaging a stent and an interior surface for engaging a delivery tube. The exterior surface has at least one fin projecting therefrom along the longitudinal axis of the band. The fin has at least one obtusely shaped surface relative to the longitudinal axis and facing one of the ends. The reconstrainment band is included in a delivery device for intraluminally positioning and deploying a radially distensible stent. Reconstrainment of a partially deployed stent is provided by the delivery device.

18 Claims, 9 Drawing Sheets

(56) References Cited

U.S. PATENT DOCUMENTS

2006/0058865 A1    3/2006   Case et al.
2006/0100688 A1    5/2006   Jordan et al.
2008/0009934 A1    1/2008   Schneider et al.

* cited by examiner

RECONSTRAINMENT BAND WITH REDUCED REMOVAL INTERFERENCE

CROSS-REFERENCE TO RELATED APPLICATIONS

The present application is a continuation of U.S. patent application Ser. No. 12/845,243, filed Jul. 28, 2010, which claims priority to U.S. patent application Ser. No. 61/229,976, filed Jul. 30, 2009, the entire contents of which are incorporated herein by reference.

FIELD OF THE INVENTION

The present invention relates generally to reconstrainment bands and, more specifically, to a reconstrainment band having reduced interference with a stent when removed therefrom.

BACKGROUND OF THE INVENTION

An endoprosthesis or intraluminal prosthesis is a medical device used in the treatment of diseased bodily lumens. One type of endoprosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, esophageal tract, tracheal/bronchial tubes and bile duct, as well as in a variety of other applications in the body. These devices are implanted within the vessel to open and/or reinforce collapsing or partially occluded sections of the lumen.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminal vascular stents, have included helically wound coils which may have undulations or zig-zags therein, slotted stents, ring stents, braided stents and open mesh wire stents. Super-elastic materials and metallic shape memory materials have also been used to form stents.

A stent may be delivered to a specific location within a body lumen by a delivery device. The delivery device includes a delivery tube on which a reconstrainment band is supported, typically in coaxial relation therewith. A tubular stent is supported on the reconstrainment band, typically in coaxial relation therewith. A tubular sheath covers the stent in coaxial relation therewith and with the delivery tube. The reconstrainment band is fixed to the delivery tube to prevent axial displacement of the reconstrainment band relative to the delivery tube. The reconstrainment band engages the stent to prevent axial displacement of the stent relative thereto. The retention of the stent by the reconstrainment band maintains the axial position of the stent relative to the reconstrainment band and delivery tube when the sheath is axially displaced relative to the delivery tube and reconstrainment band. Without the retention of the stent provided by the reconstrainment band, axial displacement of the sheath relative to the delivery tube may cause associated axial displacement of the stent as a result of frictional contact between the sheath and stent.

The retention of the stent by the reconstrainment band is beneficial during deployment of the stent by providing for the longitudinal position of the stent within the bodily lumen to be maintained during relative axial displacement of the sheath. The longitudinal position of the stent within the bodily lumen is typically significant. The maintenance of the longitudinal position of the stent relative to the delivery tube may be particularly difficult during reconstrainment. The sheath may be longitudinally retracted relative to the delivery tube such that a distal axial portion of the stent is exposed by the sheath and a proximal axial portion of the stent remains covered by the sheath. Reconstrainment refers to the forward axial displacement of the sheath relative to the delivery tube such that the axial distal portion of the stent which was uncovered by the longitudinal retraction of the sheath is recovered partially or completely by the sheath. The forward axial displacement of the sheath may cause forward longitudinal displacement of the stent relative to the delivery tube and, typically, the bodily lumen as a result of contact between the sheath and stent. Consequently, the stent may be carried by the sheath. Limiting or completely preventing such forward displacement of the stent relative to the delivery tube and bodily lumen is typically advantageous.

The partial or complete uncovering of the stent which results from the retraction of the sheath relative to the delivery tube typically results in the radial expansion of the stent in an outward direction away from the reconstrainment band. Subsequently, the delivery tube and reconstrainment band mounted thereon are retracted or longitudinally displaced in the distal direction relative to the stent for removal of the delivery tube and reconstrainment band from the stent. The radial expansion of the stent may be sufficiently limited such that the radial clearance between the interior surfaces of the stent is less than the maximum radial dimension of the fins. Consequently, the retraction or rearward longitudinal displacement of the reconstrainment band relative to the stent may result in catching of the stent by the fins. Catching of the stent by the fins may impede the removal of the reconstrainment band and the attached delivery tube from within the stent. Also, catching of the stent by the fins may cause the stent to be carried by the reconstrainment band.

Also, the reconstrainment of the stent and the initial loading thereof in the delivery device typically entails radially compressing the stent in the inward direction between the sheath and delivery tube. During the inward radial compression of the stent, it is possible for one or more of the fins to not be aligned with any of the voids in the stent into which the fins typically extend. A fin which is not aligned with any void in the stent will normally contact the interior surface of the stent as a result of the inward radial compression of the stent in the vicinity of the fin. Contact between the fin and stent may result in catching of the stent by the fin. Catching of the stent on one or more of the fins can impede the inward radial displacement of the stent toward the band and the associated inward radial compression of the stent. Consequently, the longitudinal displacement of the sheath in the distal or forward direction relative to the delivery tube which typically provides the compression of the stent is impeded. Impeding the longitudinal displacement of the sheath in the distal or forward direction relative to the delivery tube 14 interferes with the reconstrainment of the stent, and the initial loading thereof between the sheath and reconstrainment band in the delivery device.

SUMMARY OF THE INVENTION

The reconstrainment band of the present invention is used with a stent delivery device. The reconstrainment band includes a hollow generally tubular shaped band having proximal and distal ends and having an exterior surface for engaging a stent and an interior surface for engaging a delivery tube. The exterior surface has at least one fin projecting therefrom along the longitudinal axis of the band. The fin desirably has at least one obtusely shaped surface relative to the longitudinal axis and facing one of the ends. The reconstrainment band is used with the delivery device for intraluminally delivering a radially distensible stent. The delivery device includes the stent, a delivery tube around which the reconstrainment band is secured, and a sheath. The stent is located between the reconstrainment band and sheath. The delivery device is used for intraluminally positioning the stent according to a method which includes positioning the delivery device within a bodily lumen, and slidably retracting the sheath from the delivery tube to uncover a portion or all of the stent. Reconstrainment of the partially uncovered stent is provided by longitudinally displacing the sheath in a forward direction relative to the delivery tube to recover a portion or the entire uncovered portion of the stent.

The fin engages the stent when the reconstrainment band is located within the stent. The engagement of the fin with the stent resists axial displacement of the stent relative to the reconstrainment band. Consequently, when the reconstrainment band is fixed to the delivery tube, axial displacement of the stent relative to the delivery tube is obstructed. The obstruction of the axial displacement of the stent retains the axial position of the stent relative to the delivery tube. The axial position of the stent is retained by the reconstrainment band when the stent is located within a sheath and the sheath is axially displaced relative to the delivery tube. Consequently, the reconstrainment band and the fixed connection thereof to the delivery tube maintain the longitudinal position of the stent within the bodily lumen during reconstrainment.

The inclination of the obtusely shaped surface reduces the likelihood of contact between the fin and stent causing the stent to catch on the fin. Consequently, the likelihood of the catching impeding the longitudinal displacement of the reconstrainment band within the stent is reduced. As a result, removal of the reconstrainment band and the attached delivery tube from within the stent is facilitated. Also, the likelihood of the catching causing the stent to be carried by the reconstrainment band during the removal thereof from within the stent is reduced.

Additionally, the inclination of the obtusely shaped surface reduces the likelihood of the inward radial compression and displacement of the stent toward the reconstrainment band causing the stent to catch on the fin. Consequently, the likelihood of the catching impeding the reconstrainment of the stent which typically entails the inward radial compression and displacement of the stent toward the reconstrainment band is reduced. Further, the likelihood of the catching impeding the initial loading of the stent between the sheath and reconstrainment band in the delivery device which also typically entails the inward radial compression and displacement of the stent toward the reconstrainment band is reduced.

These and other features of the invention will be more fully understood from the following description of specific embodiments of the invention taken together with the accompanying drawings.

BRIEF DESCRIPTION OF THE DRAWINGS

In the drawings.

Corresponding reference characters indicate corresponding parts throughout the several views of the drawings.

DETAILED DESCRIPTION OF THE INVENTION

Figure 1:
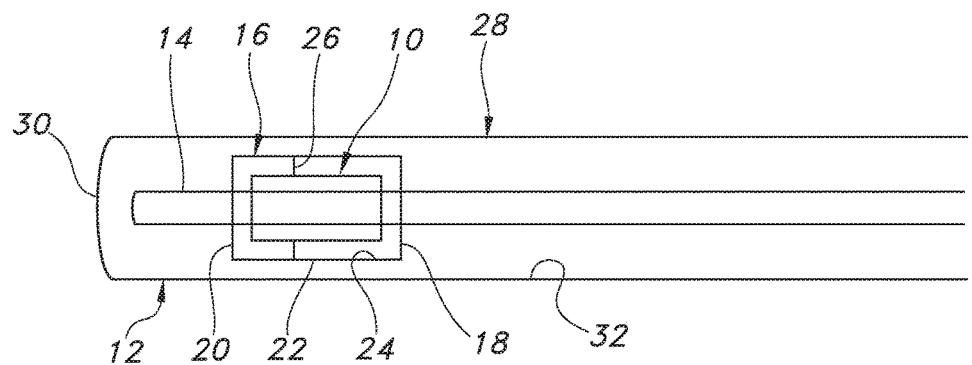
FIG. 1 is a longitudinal cross-sectional view of the reconstrainment band of the present invention showing the reconstrainment band located within a stent, the stent being shown as located within a sheath, the reconstrainment band being shown as fixed to a delivery tube located within the reconstrainment band.
Figure 1A:
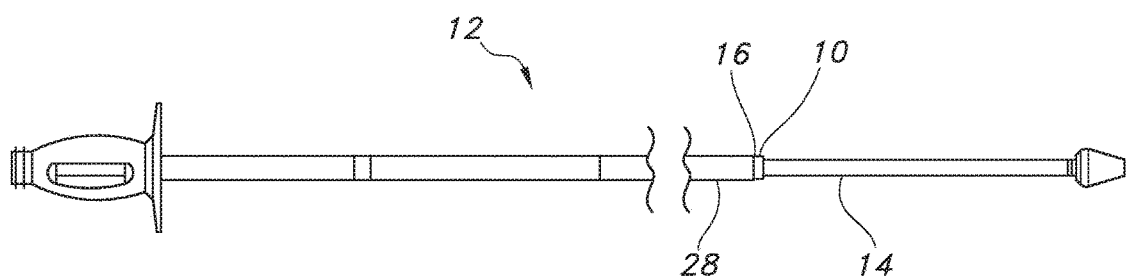
FIG. 1A is a longitudinal view of the reconstrainment band of the present invention showing the reconstrainment band located within a stent as fixed to an alternate delivery tube assembly.

Referring to the drawings and more specifically to FIGS. 1 and 1A, the reconstrainment band 10 is used with a delivery device 12. The delivery device 12 includes a delivery tube 14 on which the reconstrainment band 10 is mounted in coaxial relation therewith. The mounting of the reconstrainment band 10 on the delivery tube 14 provides for the obstruction of axial displacement of the reconstrainment band relative to the delivery tube. The mounting of the reconstrainment band 10 on the delivery tube 14 may further provide for the obstruction of transverse or rotational displacement of the reconstrainment band relative to the delivery tube.

A stent 16 is located around the reconstrainment band 10 in coaxial relation therewith. The stent 16 has a proximal end 18, a distal end 20, an exterior surface 22, and an interior surface 24.

The stent 16 is engaged by fins 26 extending radially outward from the outer surface of the reconstrainment band 10 such that axial displacement of the stent 16 relative to the reconstrainment band is obstructed. The engagement of the stent 16 by the fins 26 may further obstruct transverse or rotational displacement of the stent relative to the reconstrainment band.

The delivery device 12 may include a tubular sheath 28 which is located circumferentially around the stent 16 in coaxially relation therewith. The sheath 28 has a distal end 30 and an interior surface 32.

The delivery device 12 provides for the deployment of the stent 16 to a location within a body lumen by positioning the stent around and in engagement with the reconstrainment band 10 such that axial displacement of the stent relative to the reconstrainment band is obstructed.

The sheath 28 is located around the stent 16 in coaxial relation therewith such that the stent is at least partially covered in the axial direction by the sheath. The sheath 28 may completely cover the stent 16, if desired. When the stent 16 and sheath 28 are apart from one another and substantially no transverse force is applied to either, the transverse dimension of the exterior surface 22 of the stent is larger than the transverse dimension of the interior surface 32 of the sheath. The sheath 28 resists outward radial expansion to a greater degree relative to the resistance of the stent 16 to inward radial compression. Consequently, the stent 16 is radially compressed in the inward direction when the sheath 28 is located around the stent.

Figure 2:
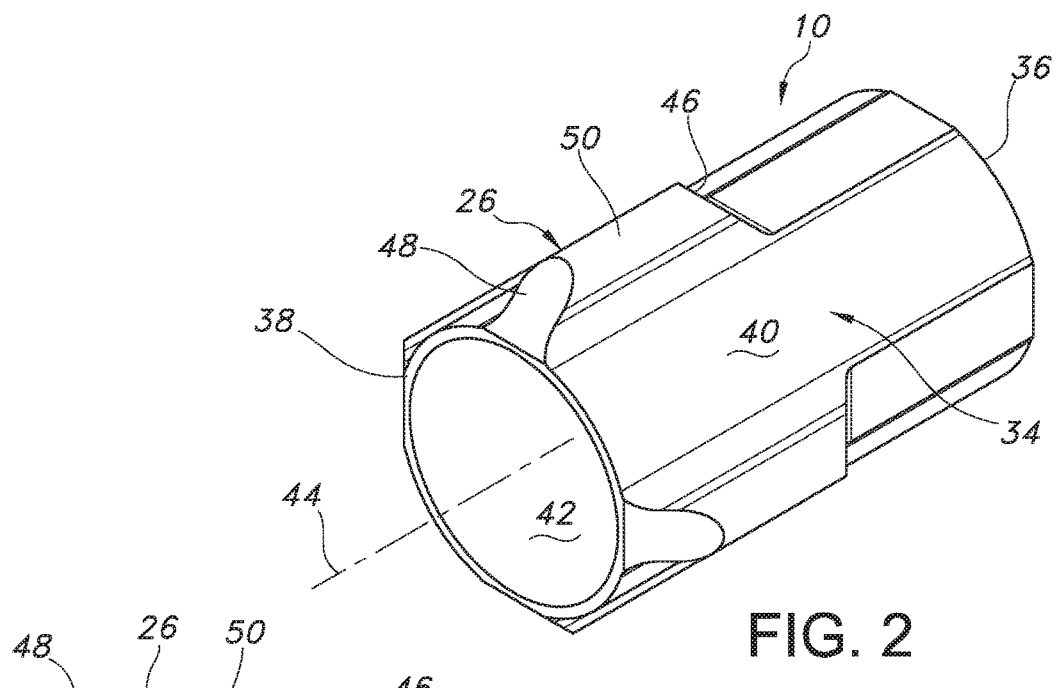
FIG. 2 is a perspective view of the reconstrainment band of FIG. 1.
Figure 3:
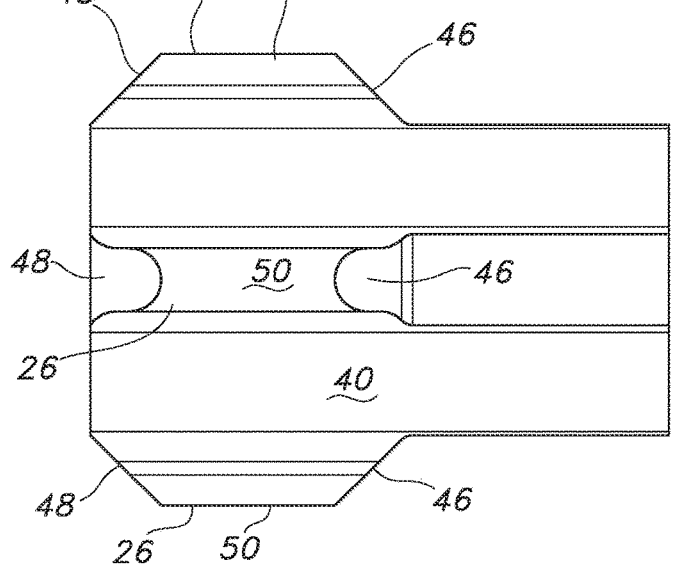
FIG. 3 is a longitudinal cross-sectional view of the reconstrainment band of FIG. 2.
Figure 4:
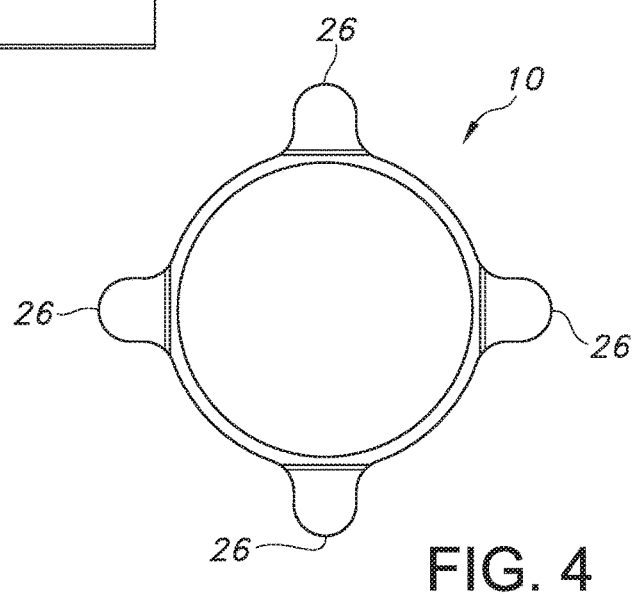
FIG. 4 is a left end elevational view of the reconstrainment band of FIG. 3.

As shown in FIGS. 2 to 4, the reconstrainment band 10 includes a hollow, generally tubular shaped band 34 having a proximal end 24 and a distal end 38. The band 34 has an exterior surface 40 for engaging the stent 16. The band 34 has an interior surface 42 for engaging the delivery tube 14. The exterior surface 40 has a plurality of fins 26 projecting radially outward therefrom along the longitudinal axis 44 of the band 34. The fins 26 are integrally connected to the band 34.

The fins 26 each extend longitudinally in the same direction as the longitudinal axis 44. Desirably, the band 34 includes an even number of fins 26, such that the fins are included in pairs. The fins 26 are desirably located relative to a transverse plane through the band 34 such that adjacent pairs of fins are separated by arcuate dimensions which are the same. For example, when two fins 26 are included, they are desirably separated by about 180°.

The fins 26 each have an obtusely shaped surface 46 relative to the longitudinal axis 44. The obtusely shaped surface 46 faces the proximal end 36. The obtusely shaped surface 46 intersects the exterior surface 40 at a location which is longitudinally offset in the distal direction relative to the proximal end 36 of the band 34.

Figure 23:
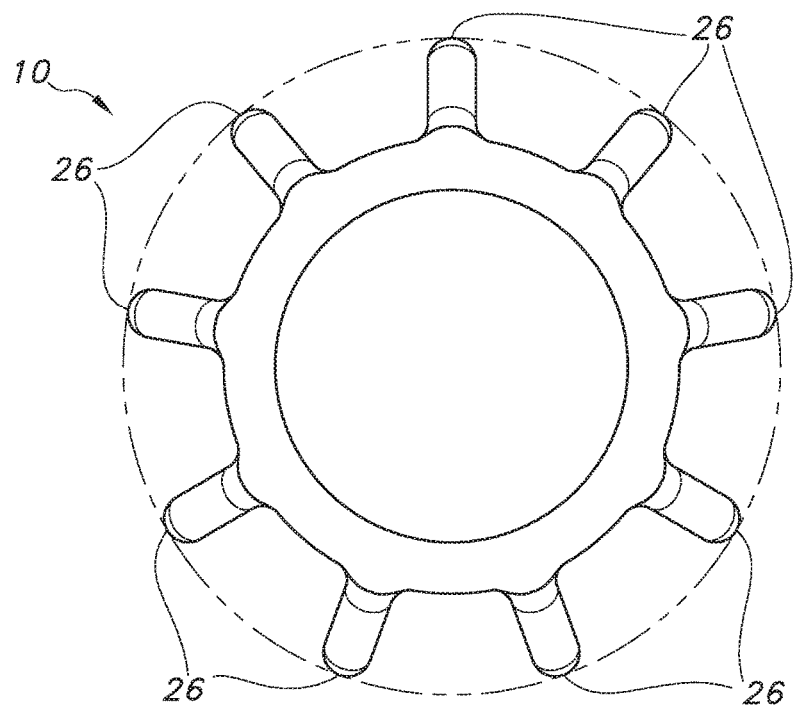
FIG. 23 is a left end elevational view of an alternate embodiment of a reconstrainment band.
Figure 24:
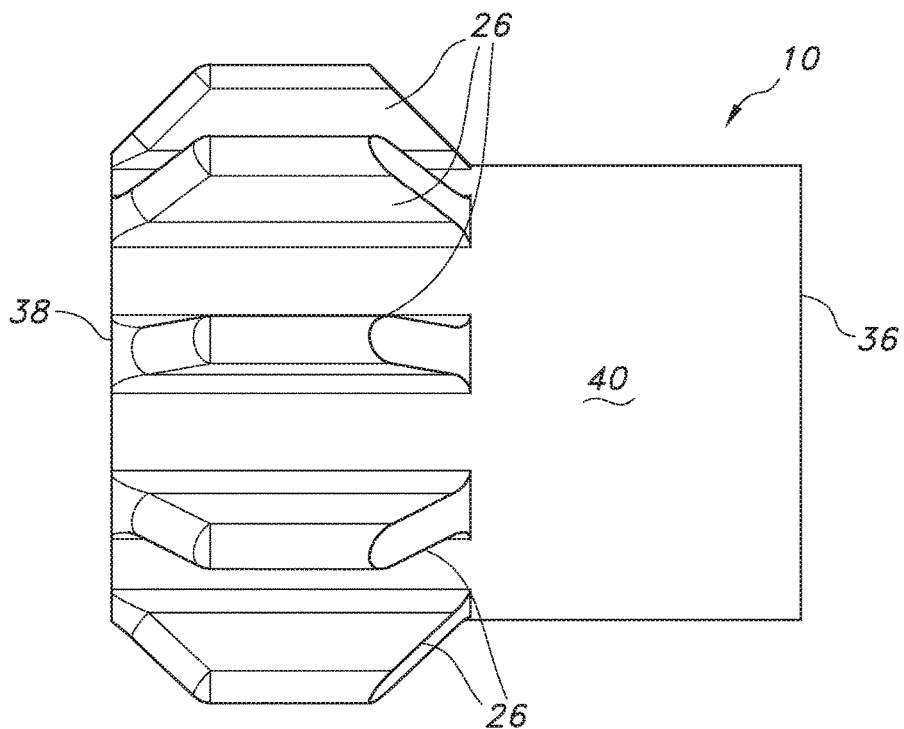
FIG. 24 is a longitudinal cross-sectional view of the reconstrainment band of FIG. 23.

The fins 26 each have an obtusely shaped surface 48 relative to the longitudinal axis 44. The obtusely shaped surface 48 faces the distal end 38. The obtusely shaped surface 48 intersects the exterior surface 40 at a location near to the distal end 38 of the band 34. Any number of fins 26 may be included on the band 34. For example, the band 34 may include any number of fins from 1 to 10 fins. As depicted in FIGS. 23-24, for example, the reconstrainment band may include nine fins 26 spaced around the exterior surface of the band 34. Desirably, each fin 26 is spaced about 40° away from each other, such that each fin is separated by an equal distance around the periphery of the band 34.

The fins 26 each have an exterior surface 50 which extends between the obtusely shaped surfaces 46, 48. The exterior surface 50 faces radially outward from the band 34. The obtusely shaped surfaces 46, 48 most desirably form about a 45° angle with the surface 40 of the reconstrainment band 10. If desired, the fins 26 may have substantially rounded edges. The contour of the exterior surface 50 is preferably continuous.

The reconstrainment band 10 and its components may be formed of expanded polytetrafluoroethylene (ePTFE) or polyurethane. The reconstrainment band 10 may be formed of biocompatible materials, such as biocompatible polymers including those which are known. Such polymers may include fillers such as metals, carbon fibers, glass fibers or ceramics. Also, such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the reconstrainment band 10. In alternative embodiments, the reconstrainment band 10 may be formed from a polymer sleeve.

The reconstrainment band 10 may optionally be formed of materials such as nitinol, Elgiloy, stainless steel, cobalt chromium, including M P 3 5N, cobalt-based alloy, tantalum, niobium, platinum, gold, titanium, combinations thereof and other biocompatible metals, polymers and materials. Additionally, the reconstrainment band 10 may include structural members which have an inner core formed of tantalum, gold, platinum, iridium, or a combination thereof, and an outer cladding of nitinol to provide composite members for improved radio-opacity or visibility. Examples of such composite members are disclosed in U.S. Patent Application Publication No. 2002/0035396 which is hereby incorporated by reference herein.

The reconstrainment band 10 maybe treated with anti-thrombogenic agents (such as heparin, heparin derivatives, urokinase, and PPack (dextrophenylalanine proline arginine chloroinethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/ antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The reconstrainment band 10 is preferably secured to the delivery tube 14 of the delivery device 12 such that the reconstrainment band is located around the delivery tube in coaxial relation therewith. The reconstrainment band 10 may be removably secured to the delivery tube, if desired. The securing of the reconstrainment band 10 to the delivery tube 14 obstructs axial displacement of the reconstrainment band relative to the delivery tube. The securing of the reconstrainment band 10 to the delivery tube 14 may further provide for obstruction of transverse or rotational displacement of the reconstrainment band relative to the delivery tube.

The stent 16 may be located around the reconstrainment band 10 in coaxial relation therewith. The stent 16 has one or more voids in which the fins 26 extend to obstruct axial displacement of the stent 16 relative to the reconstrainment band 10. Consequently, axial displacement of the stent 16 relative to the delivery tube 14 is obstructed. The sheath 28 of the delivery device 12 is located around the stent 16 in coaxial relation therewith.

During longitudinal displacement of the sheath 28 relative to the delivery tube 14, possible longitudinal displacement of the stent 16 associated with the sheath is resisted by the fins 26 which extend into the one or more voids in the stent. Consequently, the axial position of the stent 16 relative to the delivery tube 14 is maintained such that longitudinal retraction of the sheath 28 relative to the delivery tube may provide for the uncovering of an axial portion or the entire outer surface of the stent which was previously covered by the sheath. Also, the maintenance of the axial position of the stent 16 relative to the delivery tube 14 which is provided by the extension of the fins 26 into the one or more voids in the stent results in forward longitudinal displacement of the sheath 28 relative to the delivery tube enabling the sheath to cover an axial portion of the stent or the entire stent. The recovering of the stent 16 by the sheath 28 is referred to as reconstrainment of the stent.

Uncovering of the outer surface of the stent 16 results in the radial expansion of the stent away from the band 34. The sheath 28 may be sufficiently refracted relative to the stent 16 such that the distal end 30 is located proximally relative to the proximal end 30. The proximal location of the distal end 30 relative to the proximal end 18 results in the radial expansion of the entire stent 16 away from the band 34.

Alternatively, the sheath 28 may be retracted from a position in which the distal end 30 is located distally relative to the proximal end 18 to a position in which the distal end 30 is closer to the proximal end 18 but still located distally thereof. Consequently, an axial portion of the stent 16 is uncovered by the sheath 28 resulting in the radial expansion of the uncovered portion of the stent. The sheath 28 may be displaced distally relative to the delivery tube 14 such that the distal end 30 is moved closer to the distal end 20 of the stent 16. Consequently, an axial portion of the stent 16 is recovered by the sheath 28 resulting in the inward radial compression of the recovered portion of the stent. The recovering of the stent 16 by the sheath 28 requires the axial position of the stent 16 relative to the delivery tube 14 to be maintained during the distal or forward longitudinal displacement of the sheath 28 relative to the delivery tube. The axial position of the stent 16 relative to the delivery tube 14 is maintained by the extension of the fins 26 into the voids in the stent 16.

The stent 16 may be loaded in the delivery device 12 by locating the stent around the reconstrainment band 10 in coaxial relation therewith. The sheath 28 may then be located around the delivery tube 14 in coaxial relation therewith such that the distal end 30 has a proximal location relative to the proximal end 18. The sheath 28 is then longitudinally displaced in the distal direction relative to the delivery tube 14 such that the distal end 30 engages the proximal end 18. Before the engagement between the proximal and distal ends 18, 30, the proximal end 18 is radially compressed in the inward direction sufficiently such that following the engagement of the distal end 30 with the proximal end 18, the interior surface 32 rides up on the exterior surface 22 such that continued distal or forward longitudinal displacement of the sheath 28 relative to the delivery tube 14 results in the inward radial compression of the axial portion of the stent 16 which is within the sheath. The inward radial compression of the stent 16 by the sheath 28 results in the fins 26 extending in the radial direction into the voids in the stent. Typically, the distal or forward longitudinal displacement of the sheath 28 relative to the delivery tube 14 is sufficient such that the distal end 30 has a longitudinal position relative to the delivery tube which coincides with the distal end 20 resulting in the entire stent 16 being located within the sheath.

The delivery device 12, including the stent 16 located between the sheath 28 and delivery tube 14, is inserted into and through a bodily lumen and displaced therein such that the stent is positioned at a desired location within the bodily lumen. When the delivery device 12 has positioned the stent 16 at the desired location within the body lumen, the stent is released from the delivery device 12 by maintaining the position of the delivery tube 14 within the bodily lumen and retracting or proximally displacing the sheath 28 relative to the delivery tube to uncover the stent. The sheath 28 is sufficiently retracted or rearwardly displaced relative to the delivery tube 14 such that the distal end 30 has a proximal or rearward location relative to the proximal end 18 of the stent 16. Consequently, the entire stent 16 radially expands away from the band 34 and engages the inner surface of the bodily lumen, typically, for implantation therein. During the retraction of the sheath 28, the axial position of the stent 16 relative to the delivery tube 14 is maintained by the engagement of the stent by the fins 26 of the reconstrainment band 10. The engagement between the fins 26 and the stent 16 resists the stent from being carried by the sheath 28 in the direction of the retraction thereof. The stent 16 is thereby deployed from the delivery device 12 into the bodily lumen.

Following the radial expansion of the entire stent 16, the delivery tube 14 and reconstrainment band 10 mounted thereon are retracted or longitudinally displaced in the distal direction relative to the stent for removal of the delivery tube and reconstrainment band from the bodily lumen. The radial expansion of the stent 16 may be sufficiently limited such that the radial clearance between the interior surface 24 is less than the maximum radial dimension of the fins 26. Consequently, the retraction or rearward longitudinal displacement of the reconstrainment band 10 relative to the stent 16 may result in contact between the obtusely shaped surfaces 46 and stent 16. The inclination of the obtusely shaped surfaces 46 reduces the likelihood of the contact between the fins 26 and stent 16 resulting in catching of the stent by the fins. Catching of the stent 16 by the fins 26 may impede the removal of the reconstrainment band 10 and the attached delivery tube 14 from the bodily lumen. Also, catching of the stent 16 by the fins 26 may dislodge the stent from the inner surface of the bodily lumen and displace the stent relative thereto.

Following the loading of the stent 16 in the delivery device 12, and the insertion and displacement thereof through a bodily lumen such that the stent is positioned at the desired location in the bodily lumen, the sheath 28 may be retracted or longitudinally displaced in the rearward direction relative to the delivery tube 14 such that the distal end 30 remains positioned distally relative to the proximal end 18. Consequently, retraction of the sheath 28 uncovers an axial portion of the stent 16 resulting in the radial expansion of the uncovered axial portion thereof. The radial expansion of the stent 16 results in the radial displacement of the sections thereof which are adjacent to the fins 26 toward the ends thereof. The radial displacement of the stent 16 may be sufficient such that the ends of the fins 26 are located adjacent to the interior surface 24 of the stent. Subsequently, the sheath 28 may be displaced in the distal or longitudinally forward direction relative to the delivery tube 14 such that a portion or the entire uncovered axial portion of the stent 16 is recovered by the sheath. During the recovering of the stent 16 or reconstrainment, the axial position of the stent relative to the reconstrainment band 10 and delivery tube 14 is maintained by the engagement of the stent by the fins 26. The engagement between the fins 26 and stent 16 obstructs the stent from being carried by the sheath 28 in the distal or longitudinally forward direction relative to the delivery tube 14. Reconstrainment may be required after determining that further displacement of the delivery device 12 within the body lumen is necessary to position the stent 16 at a different location within the body lumen. The axial portion of the stent 16 which is recovered by the sheath 28 is radially compressed in the inward direction by the sheath.

The radial expansion of the stent 16 and longitudinal displacement of the sheath 28 may cause one or more of the fins 26 to become displaced from alignment with the voids in the stent. A fin 26 which is not aligned with any void in the stent 16 will normally contact the interior surface 24 as a result of the inward radial compression of the stent in the vicinity of the fin. The inclination of the obtusely shaped surfaces 46, 48 reduces the likelihood of contact between the fins 26 and interior surface 24 causing the stent 16 to catch on the fins 26. Catching of the stent 16 on one or more of the fins 26 can impede the inward radial displacement of the stent toward the band 34 and the associated inward radial compression of the stent. Consequently, the longitudinal displacement of the sheath 28 in the distal or forward direction relative to the delivery tube 14 is impeded. Impeding the longitudinal displacement of the sheath 28 in the distal or forward direction relative to the delivery tube 14 interferes with the reconstrainment of the stent 16, and with the initial loading thereof between the sheath and reconstrainment band 10 in the delivery device 12.

Figure 5:
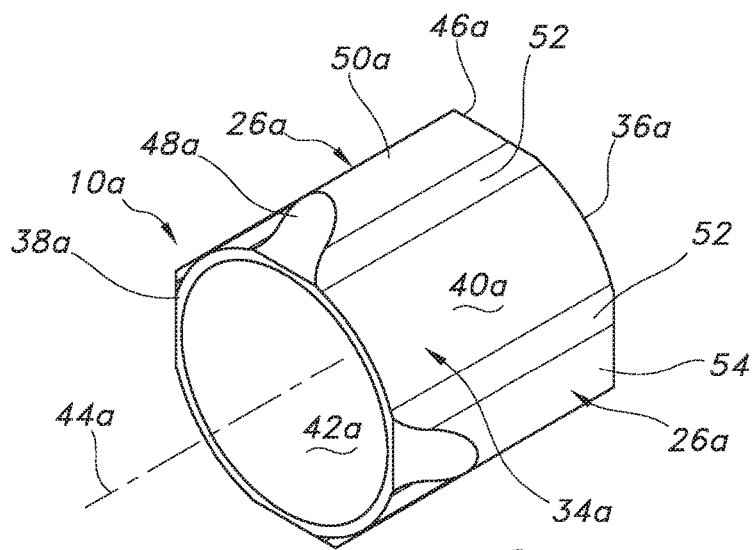
FIG. 5 is a perspective view of an alternative embodiment of the reconstrainment band of FIG. 1.
Figure 6:
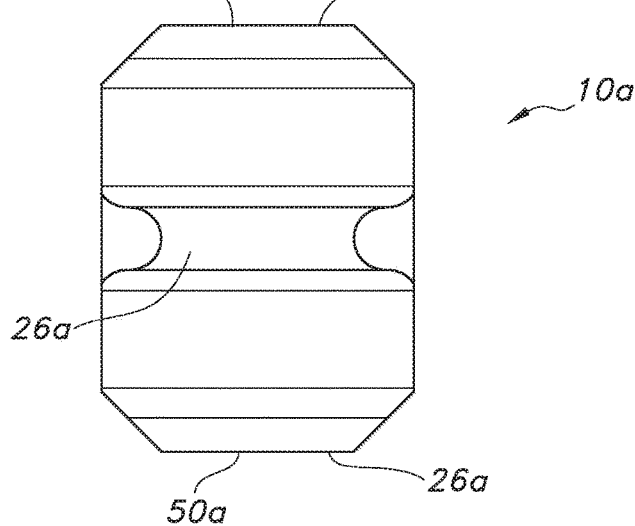
FIG. 6 is a longitudinal cross-sectional view of the reconstrainment band of FIG. 5.
Figure 7:
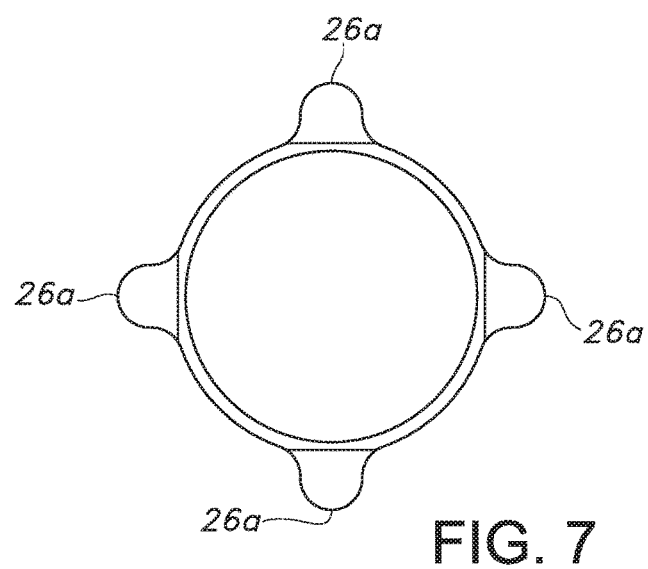
FIG. 7 is a left end elevational view of the reconstrainment band of FIG. 6.

An alternative embodiment of the reconstrainment band 10a is shown in FIGS. 5 to 7. Parts illustrated in FIGS. 5 to 7 which correspond to parts illustrated in FIGS. 1 to 4 have, in FIGS. 5 to 7, the same reference numeral as in FIGS. 1 to 4 with the addition of a suffix "a". In this alternative embodiment, the reconstrainment band 10a has four fins 26a. The fins 26a extend longitudinally in the same direction as the longitudinal axis 44a. The fins 26a are located relative to a transverse plane through the band 34a such that the adjacent pairs of fins are separated by arcuate dimensions which are the same. The obtusely shaped surfaces 46a intersect the exterior surface 40a at the proximal end 36a of the band 34a. The obtusely shaped surfaces 48a intersect the exterior surface 40a at the distal end 38a of the band 34a.

The exterior surfaces 50a each have a pair of lateral regions 52 which intersect the exterior surface 40a of the band 34a on opposite sides of the corresponding fin 26a, as shown in FIGS. 5 and 7. The lateral regions 52 extend longitudinally in a direction which is parallel to the longitudinal axis 44a. The lateral regions 52 each have corresponding contours which differ from the contour of the exterior surface 40a such that the intersections between the lateral regions and exterior surface define discontinuities. The exterior surfaces 50a each have a shoulder region 54 which is located between the corresponding lateral regions 52, as shown in FIG. 5. The shoulder regions 54 each extend longitudinally in a direction which is parallel to the longitudinal axis 44a. The shoulder regions 54 each have corresponding contours which differ from the contours of the lateral regions 52 such that the intersections between the shoulder and lateral regions define discontinuities.

Figure 8:
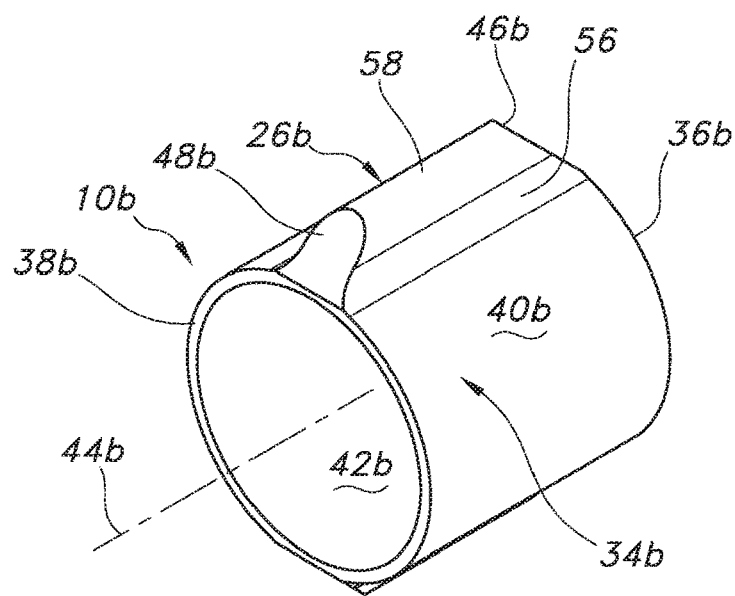
FIG. 8 is a perspective view of a further alternative embodiment of the reconstrainment band of FIG. 1.
Figure 9:
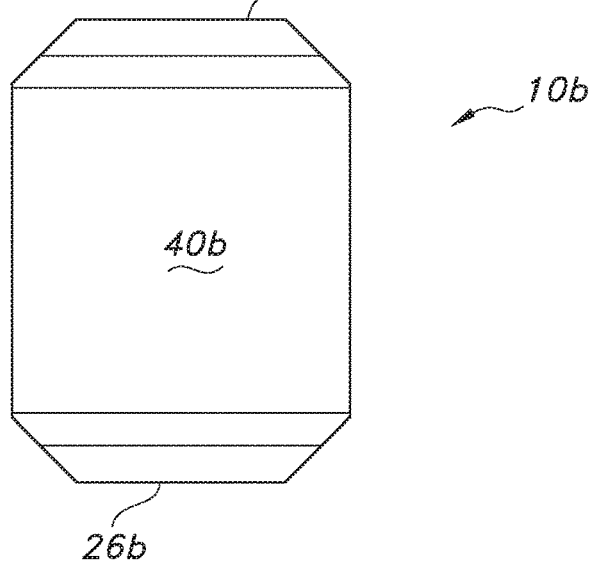
FIG. 9 is a longitudinal cross-sectional view of the reconstrainment band of FIG. 8.
Figure 10:
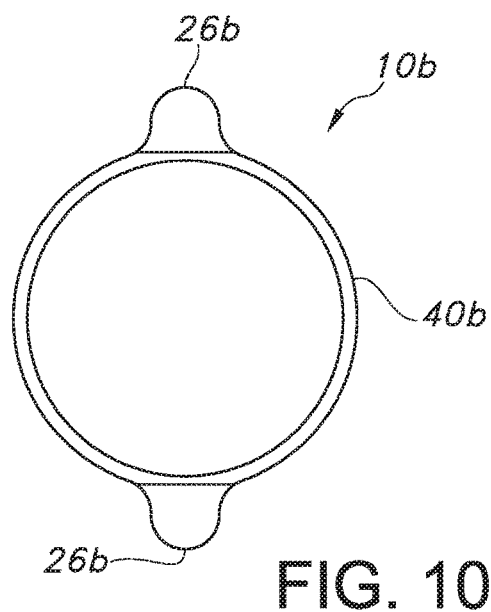
FIG. 10 is a left end elevational view of the reconstrainment band of FIG. 9.

An alternative embodiment of the reconstrainment band 10b is shown in FIGS. 8 to 10. Parts illustrated in FIGS. 8 to 10 which correspond to parts illustrated in FIGS. 1 to 4 have, in FIGS. 8 to 10, the same reference numeral as in FIGS. 1 to 4 with the addition of the suffix "b". In this alternative embodiment, the reconstrainment band 10b has a pair of fins 26b which project from diametrically opposed locations on the exterior surface 40b. The fins 26b extend longitudinally in the same direction as the longitudinal axis 44b. The obtusely shaped surfaces 46b intersect the exterior surface 40b at the proximal end 36b of the band 34b. The obtusely shaped surfaces 48b intersect the exterior surface 40b at the distal end 38b of the band 34b.

The exterior surfaces 50b each have a pair of lateral regions 56 which intersect the exterior surface 40b of the band 34b on opposite sides of the corresponding fin 26b, as shown in FIGS. 8 and 10. The lateral regions 56 extend longitudinally in a direction which is parallel to the longitudinal axis 44b. The lateral regions 56 each have corresponding contours which differ from the contour of the exterior surface 40b such that the intersections between the lateral regions and exterior surface define discontinuities. The exterior surfaces 50b each have a shoulder region 58 which is located between the corresponding lateral regions 56, as shown in FIG. 8. The shoulder regions 58 each extend longitudinally in a direction which is parallel to the longitudinal axis 44b. The shoulder regions 58 each have corresponding contours which differ from the contours of the lateral regions 56 such that the intersections between the shoulder and lateral regions define discontinuities.

Figure 11:
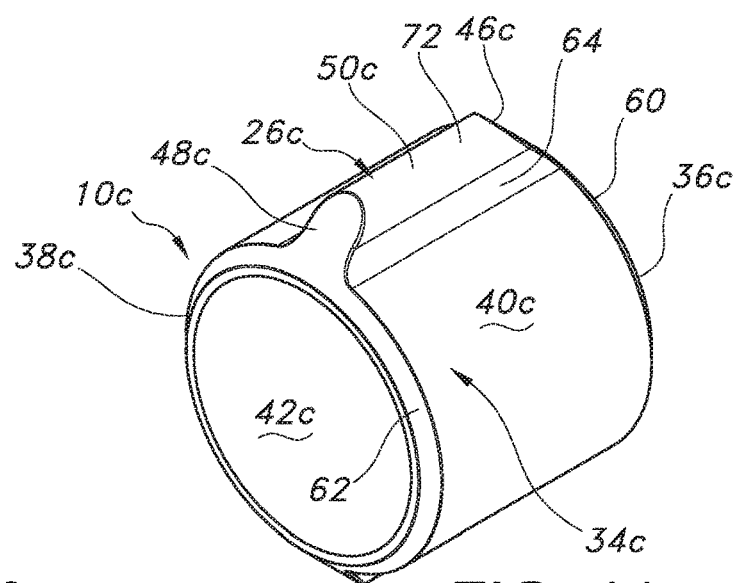
FIG. 11 is a perspective view of a further alternative embodiment of the reconstrainment band of FIG. 1.
Figure 12:
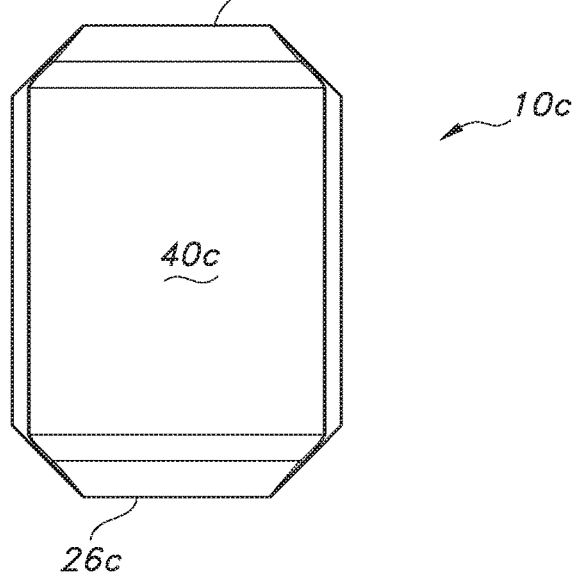
FIG. 12 is a longitudinal cross-sectional view of the reconstrainment band of FIG. 11.
Figure 13:
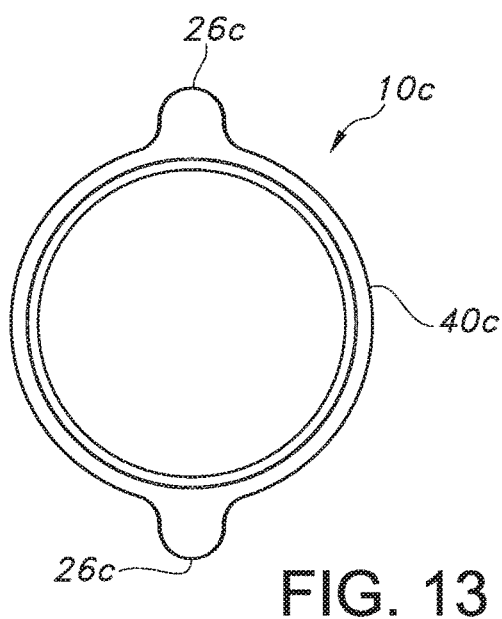
FIG. 13 is a left end elevational view of the reconstrainment band of FIG. 12.

An alternative embodiment of the reconstrainment band 10c is shown in FIGS. 11 to 13. Parts illustrated in FIGS. 11 to 13 which correspond to parts illustrated in FIGS. 1 to 4 have, in FIGS. 11 to 13, the same reference numeral as in FIGS. 1 to 4 with the addition of a suffix "c". In this alternative embodiment, the reconstrainment band 10c has a pair of fins 26c which project from diametrically opposed locations on the exterior surface 40c. The band 34c has a proximal intermediate end surface 60 which is circular and located between the proximal end 36c and exterior surface 40c. The proximal intermediate end surface 60 has a contour which is the same as the contour of the obtusely shaped surface 46c. Consequently, the intersection between the exterior surface 40c and proximal intermediate end surface 60 defines a discontinuity.

The band 34c has a distal intermediate end surface 62 located between the distal end 38c and exterior surface 40c. The distal intermediate end surface 62 is circular and has a contour which is the same as the obtusely shaped surface 48c. Consequently, the intersection between the exterior surface 40c and distal intermediate end surface 64 defines a discontinuity.

The exterior surfaces 50c each have a pair of lateral regions 64 which intersect the exterior surface 40c of the band 34c on opposite sides of the corresponding fin 26c, as shown in FIGS. 11 and 13. The lateral regions 64 each extend longitudinally in a direction which is parallel to the longitudinal axis 44c. The lateral regions 64 each have corresponding contours which differ from the contour of the exterior surface 40c such that the intersections between the lateral regions 64 and exterior surface define discontinuities. The exterior surfaces 50c each have a shoulder region 66 which is located between the corresponding lateral regions 64, as shown in FIG. 11. The shoulder regions 66 each extend longitudinally in a direction which is parallel to the longitudinal axis 44c. The shoulder regions 66 each have corresponding contours which differ from the contours of the lateral regions 64 such that the intersections between the shoulder and lateral regions define discontinuities.

Figure 14:
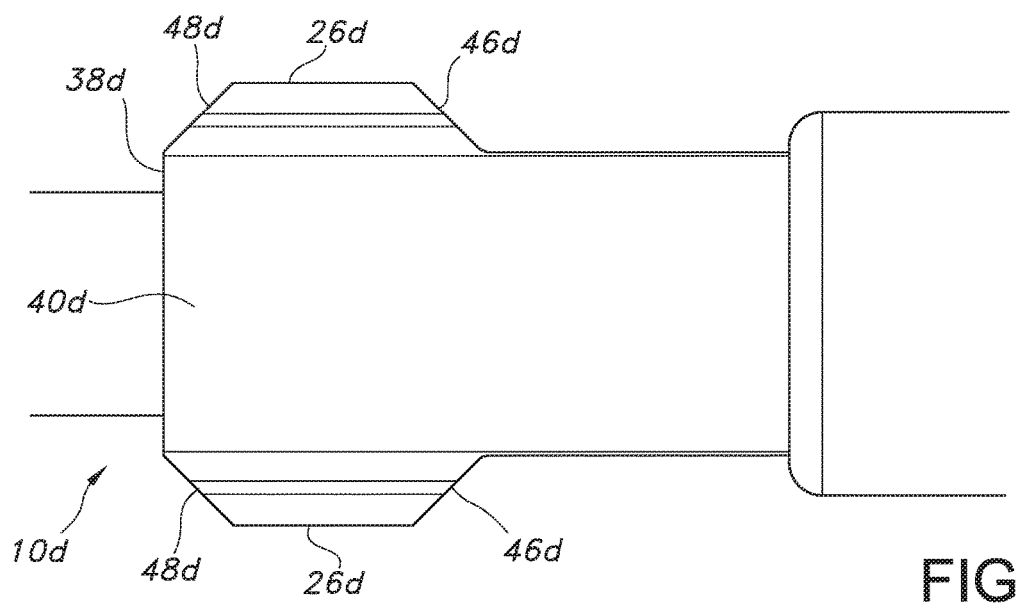
FIG. 14 is a perspective view of a further alternative embodiment of the reconstrainment band of FIG. 1.
Figure 15:
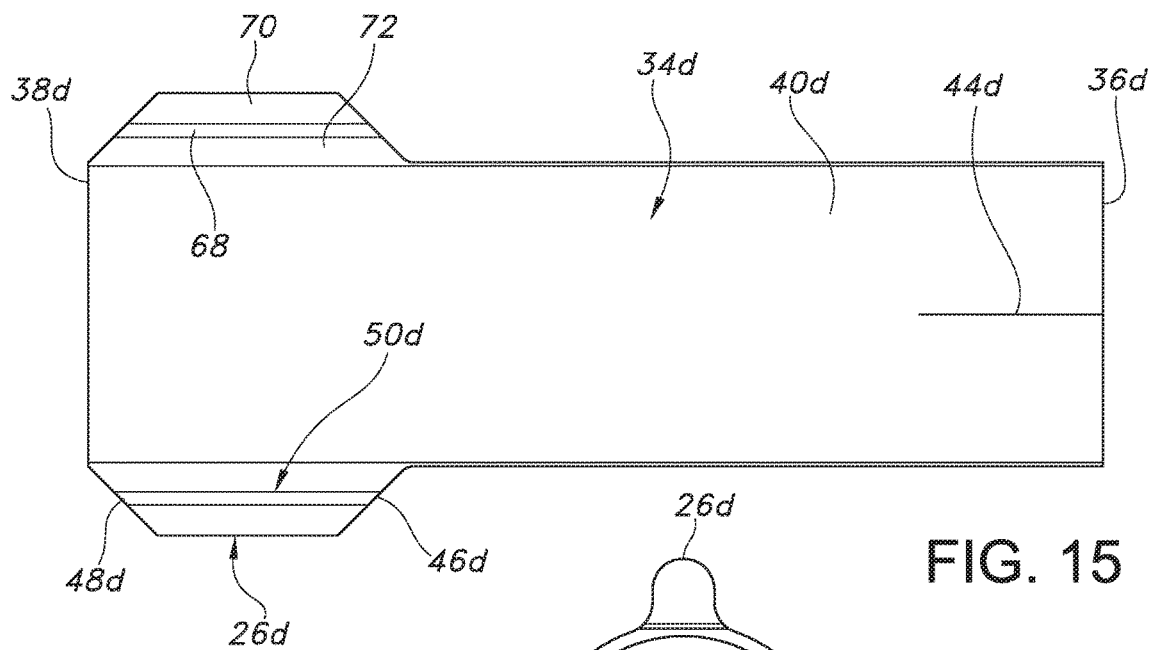
FIG. 15 is a longitudinal cross-sectional view of the reconstrainment band of FIG. 14.
Figure 16:
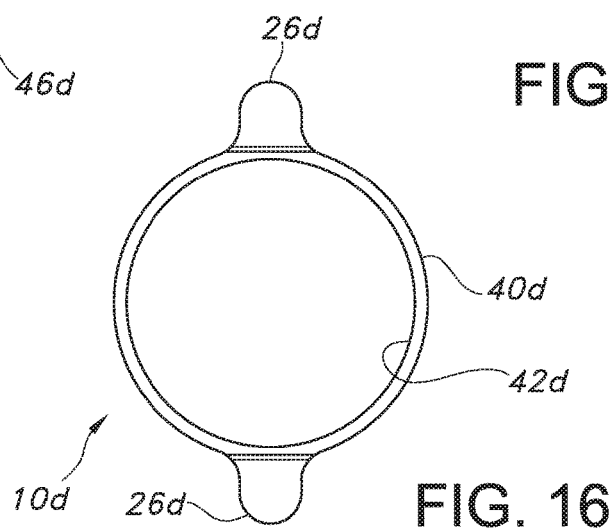
FIG. 16 is a left end elevational view of the reconstrainment band of FIG. 15.

An alternative embodiment of the reconstrainment band 10d is shown in FIGS. 14 to 16. Parts illustrated in FIGS. 14 to 16 which correspond to parts illustrated in FIGS. 1 to 4 have, in FIGS. 14 to 16, the same reference numerals as in FIGS. 1 to 4 with the addition of the suffix "d". In this alternative embodiment, the reconstrainment band 10d has a pair of fins 26d which project from diametrically opposed locations on the exterior surface 40d. The obtusely shaped surfaces 46d intersect the exterior surface 40d at a location which is longitudinally offset in the distal direction relative to the proximal end 36d of the band 34d. The obtusely shaped surfaces 48d intersect the exterior surface 40d at the distal end 38d of the band 34d.

The exterior surfaces 50d each have a pair of base lateral regions 68 which intersect the exterior surface 40d of the band 34d on opposite sides of the corresponding fin 26d, as shown in FIGS. 14 and 16. The base lateral regions 68 extend longitudinally in a direction which is parallel to the longitudinal axis 44d. The base lateral regions 68 each have corresponding contours which differ from the contour of the exterior surface 40d such that the intersections between the base lateral regions and exterior surface define discontinuities.

The exterior surfaces 50d each have a pair of intermediate lateral regions 70 which intersect the respective base lateral regions 68 on opposite sides of the corresponding fin 26d, as shown in FIGS. 14 to 16. The intermediate lateral regions 70 extend longitudinally in a direction which is parallel to the longitudinal axis 44d. The intermediate lateral regions 70 each have corresponding contours which differ from the contours of the base lateral regions 68 such that the intersections between the intermediate and base lateral regions define discontinuities. The exterior surfaces 50d each have a shoulder region 72 which is located between the corresponding intermediate lateral regions 70, as shown in FIG. 14. The shoulder regions 72 each extend longitudinally in a direction which is parallel to the longitudinal axis 44d. The shoulder regions 72 each have corresponding contours which differ from the contours of the intermediate lateral regions 70 such that the intersections between the shoulder and intermediate lateral regions define discontinuities.

Figure 17:
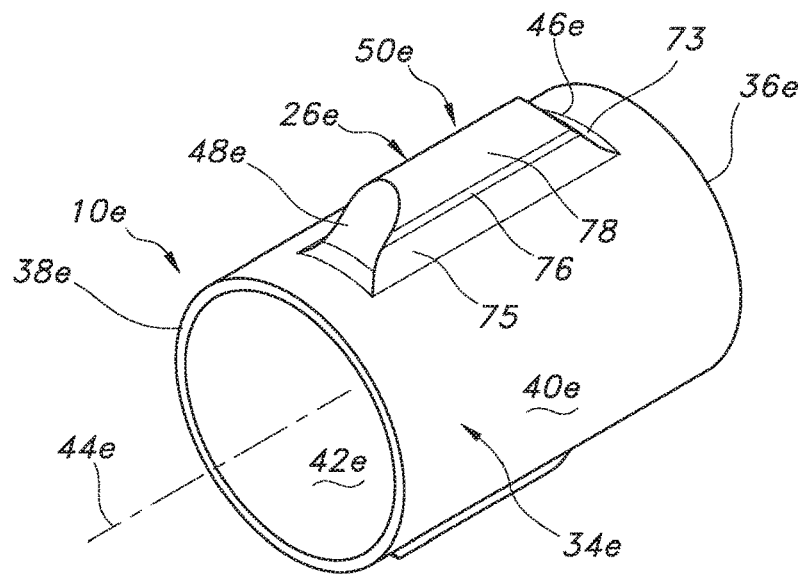
FIG. 17 is a perspective view of a further alternative embodiment of the reconstrainment band of FIG. 1.
Figure 18:
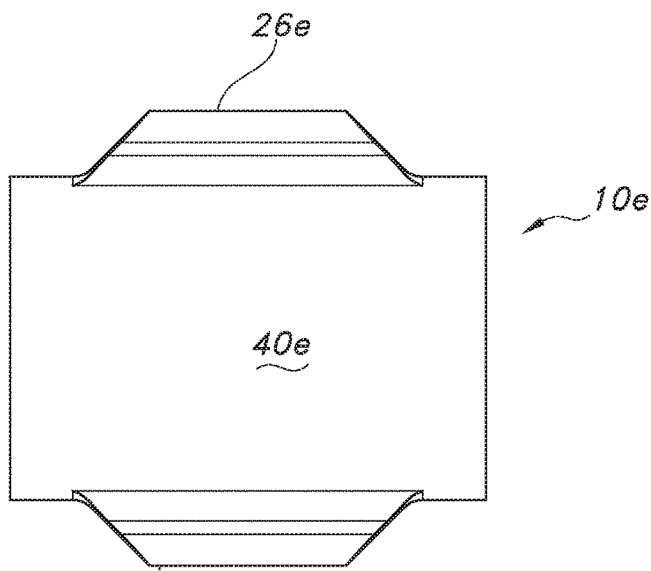
FIG. 18 is a longitudinal cross-sectional view of the reconstrainment band of FIG. 17.
Figure 19:
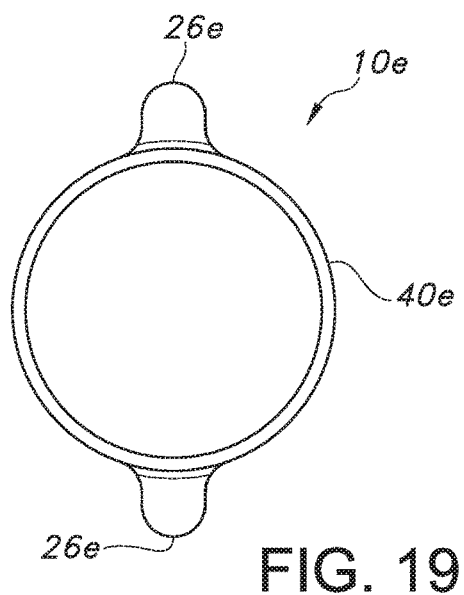
FIG. 19 is a left end elevational view of the reconstrainment band of FIG. 17.

An alternative embodiment of the reconstrainment band 10e is shown in FIGS. 17 to 19. Parts illustrated in FIGS. 17 to 19 which correspond to parts illustrated in FIGS. 1 to 4 have, in FIGS. 17 to 19, the same reference numeral as in FIGS. 1 to 4 with the addition of the suffix "e". In this alternative embodiment, the reconstrainment band 10e has a pair of fins 26e which project from diametrically opposed locations on the exterior surface 40e.

The fins 26e have respective base obtusely shaped surfaces 73 located between the first corresponding obtusely shaped surfaces 46e and the exterior surface 40e. The base obtusely shaped surfaces 73 each have corresponding contours which differ from the contours of the respective first obtusely shaped surfaces 46e such that the intersections between the base obtusely shaped surfaces and respective obtusely shaped surfaces define discontinuities. The contours of the base obtusely shaped surfaces 73 differ from the contour of the exterior surface 40e such that the intersections between the base obtusely shaped surfaces and exterior surface define discontinuities. The base obtusely shaped surfaces 73 intersect the exterior surface 40e at a location which is longitudinally offset in the distal direction from the proximal end 36e of the band 34e.

The fins 26e have respective base obtusely shaped surfaces 74 located between the corresponding second obtusely shaped surfaces 48e and the exterior surface 40e. The base obtusely shaped surfaces 74 each have corresponding contours which differ from the contours of the respective second obtusely shaped surfaces 48e such that the intersections between the base obtusely shaped surfaces and respective obtusely shaped surfaces define discontinuities. The contours of the base obtusely shaped surfaces 74 differ from the contour of the exterior surface 40e such that the intersections between the base obtusely shaped surfaces and exterior surface define discontinuities. The base obtusely shaped surfaces 74 intersect the exterior surface 40e at a location which is longitudinally offset in the proximal direction from the distal end 38e of the band 34e.

The exterior surfaces 50e each have a pair of base lateral regions 75 which each intersect the exterior surface 40e of the band 34e on opposite sides of the corresponding fin 26e, as shown in FIGS. 17 and 19. The base lateral regions 75 extend longitudinally in a direction which is parallel to the longitudinal axis 44e. The base lateral regions 75 each have corresponding contours which differ from the contours of the exterior surface 40e such that the intersections between the base lateral regions and exterior surface define discontinuities.

The exterior surfaces 50e each have a pair of intermediate lateral regions 76 which intersect the corresponding base lateral region 75 on opposite sides of the corresponding fin 26e, as shown in FIGS. 17 and 19. The intermediate lateral regions 76 extend longitudinally in a direction which is parallel to the longitudinal axis 44e. The intermediate lateral regions 76 each have corresponding contours which differ from the contours of the base lateral regions 75 such that the intersections between the intermediate and base lateral regions define discontinuities.

The exterior surfaces 50e each have a shoulder region 78 which is located between the corresponding intermediate lateral regions 76, as shown in FIG. 17. The shoulder regions 78 each extend longitudinally in a direction which is parallel to the longitudinal axis 44e. The shoulder regions 78 each have corresponding contours which differ from the contours of the intermediate lateral regions 76 such that the intersections between the shoulder and intermediate regions define discontinuities.

Figure 20:
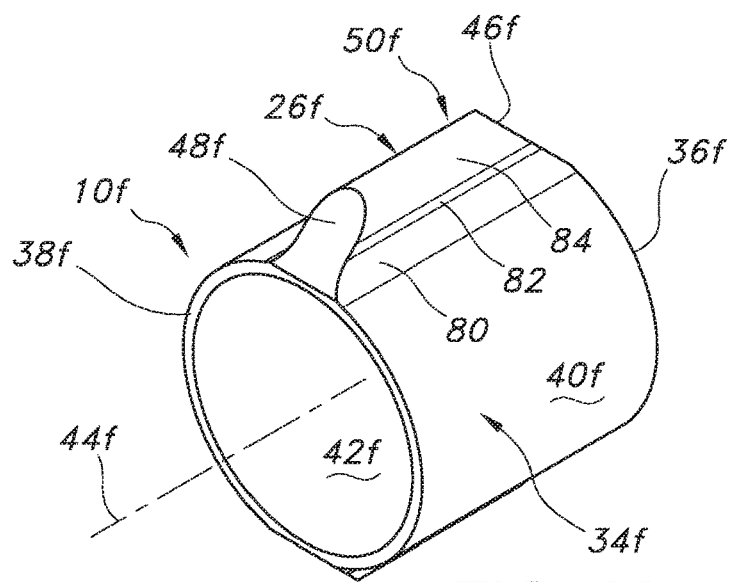
FIG. 20 is a perspective view of a further alternative embodiment of the reconstrainment band of FIG. 1.
Figure 21:
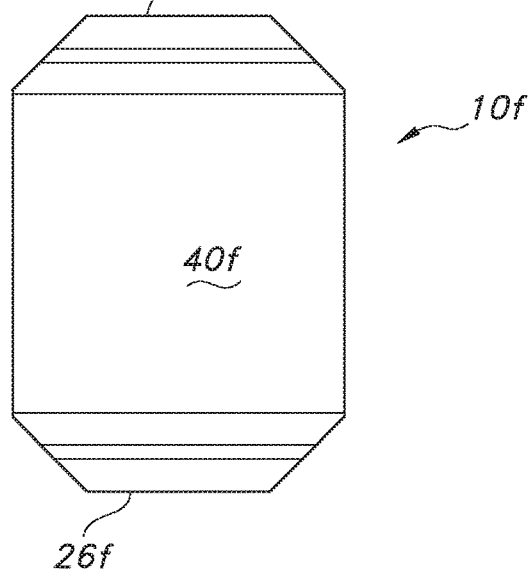
FIG. 21 is a longitudinal cross-sectional view of the reconstrainment band of FIG. 20.
Figure 22:
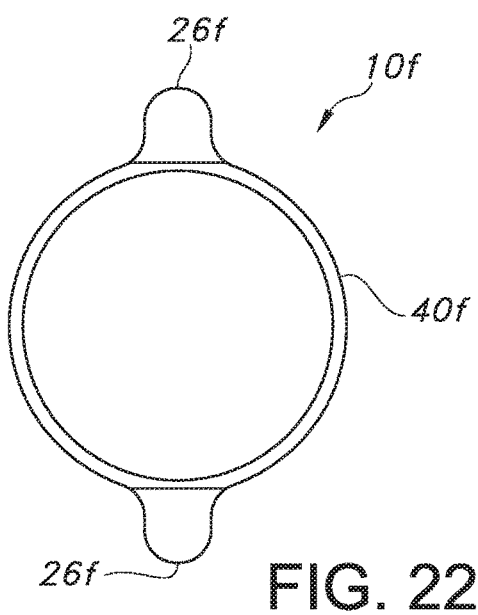
FIG. 22 is a left end elevational view of the reconstrainment band of FIG. 20.

An alternative embodiment of the reconstrainment band 10f is shown in FIGS. 20 to 22. Parts illustrated in FIGS. 20 to 22 which correspond to parts illustrated in FIGS. 1 to 4, have, in FIGS. 20 to 22, the same reference numeral as in FIGS. 1 to 4 with the addition of the suffix "f". In this alternative embodiment, the reconstrainment band 10f has a pair of fins 26f which project from diametrically opposed locations on the exterior surface 40f. First obtusely shaped surfaces 46f intersect the exterior surface 40f at the proximal end 36f of the band 34f. Second obtusely shaped surfaces 48f intersect the exterior surface 40f at the distal end 38f of the band 34f.

The exterior surfaces 50f each have a pair of base lateral regions 80 which each intersect the exterior surface 40f of the band 34f on opposite sides of the corresponding fin 26f, as shown in FIGS. 20 and 22. The base lateral regions 80 extend longitudinally in a direction which is parallel to the longitudinal axis 44f. The base lateral regions 80 each have corresponding contours which differ from the contour of the exterior surface 40f such that the intersections between the base lateral regions and exterior surface define discontinuities.

The exterior surfaces 50f each have a pair of intermediate lateral regions 82 which intersect the corresponding base lateral regions 80 on opposite sides of the corresponding fin 26f, as shown in FIGS. 20 and 22. The intermediate lateral regions 82 extend longitudinally in a direction which is parallel to the longitudinal axis 44f. The intermediate lateral regions 82 each have corresponding contours which differ from the contours of the base lateral regions 80 such that the intersections between the intermediate and base lateral regions define discontinuities.

The exterior surfaces 50f each have a shoulder region 84 which is located between the corresponding intermediate lateral regions 82, as shown in FIG. 20. The shoulder region 84 each extend longitudinally in a direction which is parallel to the longitudinal axis 44f. The shoulder regions 84 each have corresponding contours which differ from the contours of the intermediate lateral regions 82 such that the intersections between the shoulder and intermediate lateral regions define continuities.

U.S. Pat. Nos. 5,833,632, 6,014,919, 6,260,458, and 6,428,489, 6,431,039 are hereby incorporated by reference herein. Applicant's co-pending U.S. Patent Publication No. 2008/0009934 is incorporated by reference in its entirety herein.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A reconstrainment band for use with a stent delivery device, said reconstrainment band comprising:

a hollow generally tubular shaped band having proximal and distal ends and having an exterior surface for engaging a stent and an interior surface for engaging a delivery tube, said exterior surface having at least one fin projecting therefrom along a longitudinal axis of said band, said fin having a height measured perpendicular to the longitudinal axis from the exterior surface to a radially outermost extent of the at least one fin, the at least one fin including first and second opposing obtusely shaped surfaces angled relative to the longitudinal axis, the first obtusely shaped surface facing the proximal end and the second obtusely shaped surface facing the distal end, each obtusely shaped surface having rounded side and top edges, the radially outermost extent being a convexly curved surface extending between the rounded top edges of the first and second obtusely shaped surfaces, said fin comprising an exterior surface that extends longitudinally between said first and second opposing obtusely shaped surfaces, the exterior surface having a top face with a first longitudinal length radially spaced from the band, and a bottom face with a second longitudinal length adjacent the band, wherein the first longitudinal length is shorter than the second longitudinal length, wherein the first longitudinal length of the top face is longer than the height of the fin.

2. A reconstrainment band according to claim 1, wherein said fin is coupled to said band.

3. A reconstrainment band according to claim 1, wherein said fin is integral to said band.

4. A reconstrainment band according to claim 1, wherein said fin comprises a plurality of fins.

5. A reconstrainment band according to claim 4, wherein said plurality of fins comprises two opposed fins.

6. A reconstrainment band according to claim 5, wherein a first fin and a second fin of said two fins are circumferentially disposed at about 180°.

7. A reconstrainment band according to claim 1, wherein said band comprises a material selected from the group consisting of: a metal, a stainless steel, a polymer, and combinations thereof.

8. A reconstrainment band according to claim 1, wherein said fin extends longitudinally outward from said band.

9. A reconstrainment band according to claim 1, wherein the first and second opposing obtusely shaped surfaces are each angled to form a 45° angle with the exterior surface of the band.

10. A delivery device for intraluminally delivering a radially distensible stent comprising;

a delivery tube;

a reconstrainment band having a hollow generally tubular shaped band having proximal and distal ends and having an exterior surface and interior surface, the interior surface engaging the delivery tube such that the band is secured thereto, the exterior surface having at least one fin projecting therefrom along a longitudinal axis of the band, the fin having a height measured perpendicular to the longitudinal axis from the exterior surface to a radially outermost extent of the at least one fin, the at least one fin including and first and second opposing obtusely shaped surfaces angled relative to the longitudinal axis, the first obtusely shaped surface facing the proximal end and the second obtusely shaped surface facing the distal end, each obtusely shaped surface having rounded side and top edges, the radially outermost extent being a convexly curved surface extending between the rounded top edges of the first and second obtusely shaped surfaces, said fin comprising an exterior surface that extends longitudinally between said first and second opposing obtusely shaped surfaces, the exterior surface having a top face with a first longitudinal length radially spaced from the band, and a bottom face with a second longitudinal length adjacent the band, wherein the first longitudinal length is shorter than the second longitudinal length, wherein the first longitudinal length of the top face is longer than the height of the fin;

a radially distensible generally tubular shaped stent located around the band such that the fin extends into a void in the stent; and a hollow generally tubular sheath located around the stent in coaxial relation therewith, the sheath being longitudinally displaceable relative to the stent and delivery tube.

11. A delivery device for intraluminally delivering a radially expandable stent comprising;

a delivery tube having a longitudinal axis;

a reconstrainment band having a tubular shaped band having proximal and distal ends and having an exterior surface and an interior surface, the interior surface secured to the delivery tube, the exterior surface having at least one fin projecting therefrom and extending parallel to the longitudinal axis, the at least one fin having a height measured perpendicular to the longitudinal axis from the exterior surface to a radially outermost extent of the at least one fin, the at least one fin including first and second opposing obtusely shaped surfaces angled relative to the longitudinal axis, each obtusely shaped surface having a rounded upper edge, the first obtusely shaped surface facing the proximal end and the second obtusely shaped surface facing the distal end, the radially outermost extent being a convexly curved surface extending between the rounded upper edges of the first and second obtusely shaped surfaces, the at least one fin comprising a longitudinal surface that extends longitudinally between the first and second opposing obtusely shaped surfaces, the longitudinal surface having a first longitudinal length measured parallel to the longitudinal axis from the rounded upper edge of the first obtusely shaped surface to the rounded upper edge of the second obtusely shaped surface, and a second longitudinal length measured parallel to the longitudinal axis from an intersection of the first obtusely shaped surface with the exterior surface to an intersection of the second obtusely shaped surface with the exterior surface, wherein the first longitudinal length is shorter than the second longitudinal length, wherein the first longitudinal length is greater than the height of the at least one fin;

a radially expandable stent located around the reconstrainment band such that the at least one fin extends into a void in the stent; and a hollow generally tubular sheath located around the stent in coaxial relation therewith, the sheath being longitudinally displaceable relative to the stent and delivery tube.

12. The delivery device of claim 11, wherein the first and second opposing obtusely shaped surfaces are flat.

13. The delivery device of claim 12, wherein the first and second opposing obtusely shaped surfaces are each angled to form a 45° angle with the exterior surface of the band.

14. The delivery device of claim 11, wherein the rounded upper edges of the first and second obtusely shaped surfaces are spaced apart.

15. The delivery device of claim 11, wherein the at least one fin is integral to the tubular shaped band.

16. The delivery device of claim 11, wherein the at least one fin comprises a plurality of fins.

17. The delivery device of claim 16, wherein the plurality of fins comprises first and second opposing fins.

18. The delivery device of claim 17, wherein the first fin and the second fin are circumferentially disposed at about 180° apart.

* * * * *